(12) United States Patent
Katzarov et al.

(10) Patent No.: US 11,071,370 B2
(45) Date of Patent: Jul. 27, 2021

(54) HAIR INFORMATION COLLECTION DEVICE, HAIR INFORMATION COLLECTION SYSTEM, AND METHOD FOR PROVIDING HAIR CONDITION INFORMATION

(71) Applicant: Henkel AG & Co. KGaA, Duesseldorf (DE)

(72) Inventors: Jordan Katzarov, Duesseldorf (DE); Torsten Lechner, Langenfeld (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 114 days.

(21) Appl. No.: 16/471,764

(22) PCT Filed: Dec. 15, 2017

(86) PCT No.: PCT/EP2017/083148
§ 371 (c)(1),
(2) Date: Jun. 20, 2019

(87) PCT Pub. No.: WO2018/114717
PCT Pub. Date: Jun. 28, 2018

(65) Prior Publication Data
US 2019/0350343 A1 Nov. 21, 2019

(30) Foreign Application Priority Data
Dec. 22, 2016 (DE) .................... 10 2016 225 964.4

(51) Int. Cl.
*H04R 3/00* (2006.01)
*H04R 29/00* (2006.01)
(Continued)

(52) U.S. Cl.
CPC ............. *A45D 44/00* (2013.01); *A45D 24/10* (2013.01); *A46B 15/0038* (2013.01);
(Continued)

(58) Field of Classification Search
None
See application file for complete search history.

(56) References Cited

U.S. PATENT DOCUMENTS 10,426,397 B2 * 10/2019 Hutchings ............... A46B 9/023
2009/0147081 A1 * 6/2009 Hanson ............... A46B 15/0097
348/77

(Continued)

OTHER PUBLICATIONS

EPO, International Search Report and Written Opinion issued in International Application No. PCT/EP2017/083148, dated Mar. 9, 2018.

*Primary Examiner* — Peter J Macchiarolo
*Assistant Examiner* — Jermaine L Jenkins
(74) *Attorney, Agent, or Firm* — Lorenz & Kopf, LLP

(57) ABSTRACT

A hair information collection device for providing information relating to hair of a user includes a device body having at least first and second regions configured such that the hair of the user is movable between the first and second regions while in contact with the first and second regions, at least one microphone arranged in or on the device body for detecting a noise during movement of the hair between the first and second regions, a speed sensor circuit arranged in or on the device body and comprising at least one sensor for determining a value representing the speed of the device body, and an electronic circuit device arranged in or on the device body, wherein the electronic circuit device is configured to provide the user with information regarding the hair based on the received detected noise and the speed of the device body.

18 Claims, 9 Drawing Sheets

(51) Int. Cl.
*H04R 1/40* (2006.01)
*H04R 1/02* (2006.01)
*G10L 25/51* (2013.01)
*G06Q 30/06* (2012.01)
*G06F 3/14* (2006.01)
*G01N 29/14* (2006.01)
*A61B 5/00* (2006.01)
*A46B 15/00* (2006.01)
*A45D 44/00* (2006.01)
*A45D 24/10* (2006.01)

(52) U.S. Cl.
CPC ......... *A46B 15/0055* (2013.01); *A61B 5/448* (2013.01); *G01N 29/14* (2013.01); *G06F 3/14* (2013.01); *G06Q 30/0631* (2013.01); *G10L 25/51* (2013.01); *H04R 1/028* (2013.01); *H04R 1/406* (2013.01); *H04R 3/005* (2013.01); *H04R 29/005* (2013.01); *A45D 2044/007* (2013.01); *A46B 2200/104* (2013.01)

(56) References Cited

U.S. PATENT DOCUMENTS

| | | | |
|---|---|---|---|
| 2015/0164407 A1* | 6/2015 | Hyde | A61B 5/742 |
| | | | 600/301 |
| 2015/0342515 A1 | 12/2015 | Hutchings et al. | |
| 2017/0164887 A1* | 6/2017 | Chattopadhyay | A42B 3/0433 |

* cited by examiner

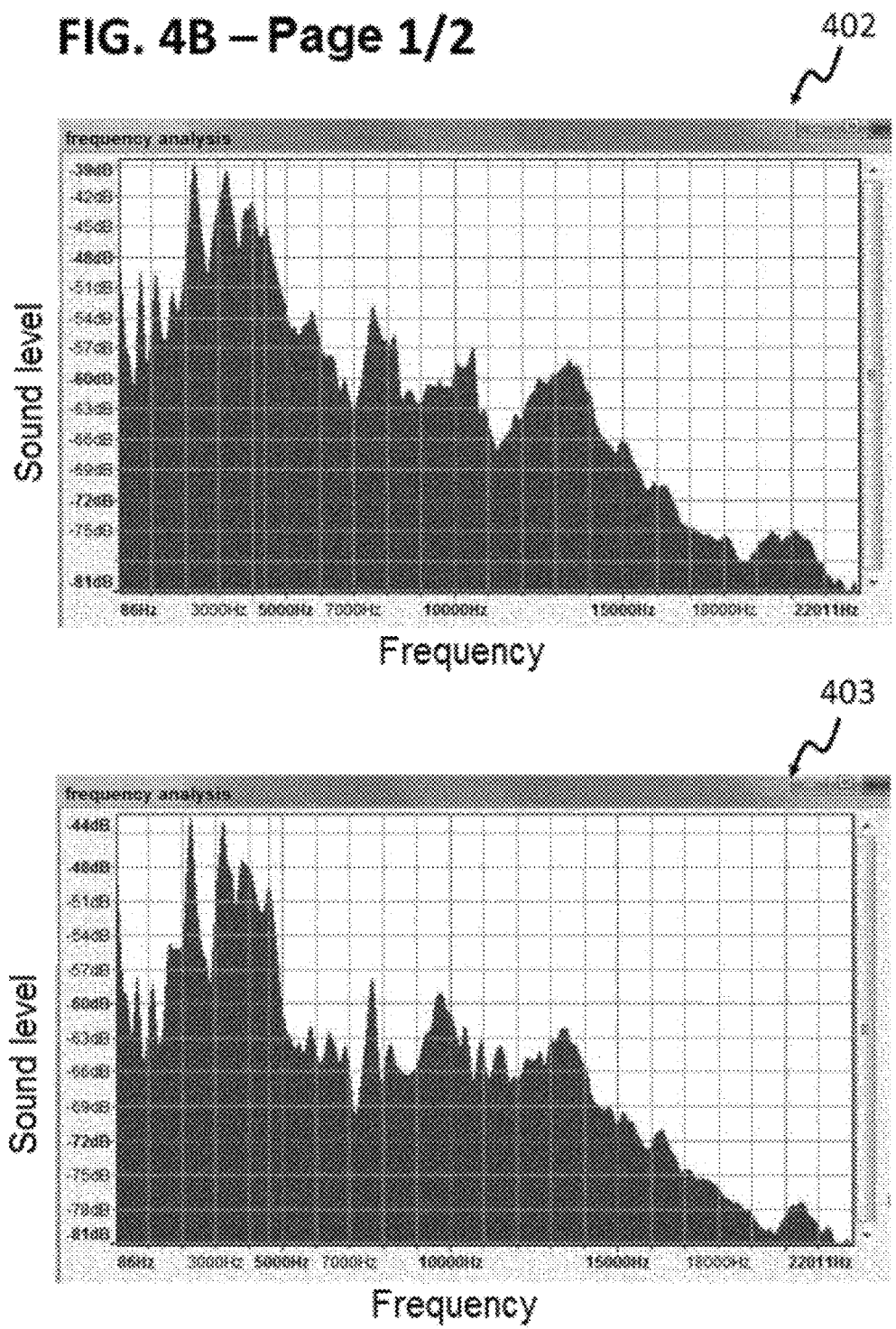
FIG. 4B – Page 1/2

FIG. 4B – Page 2/2
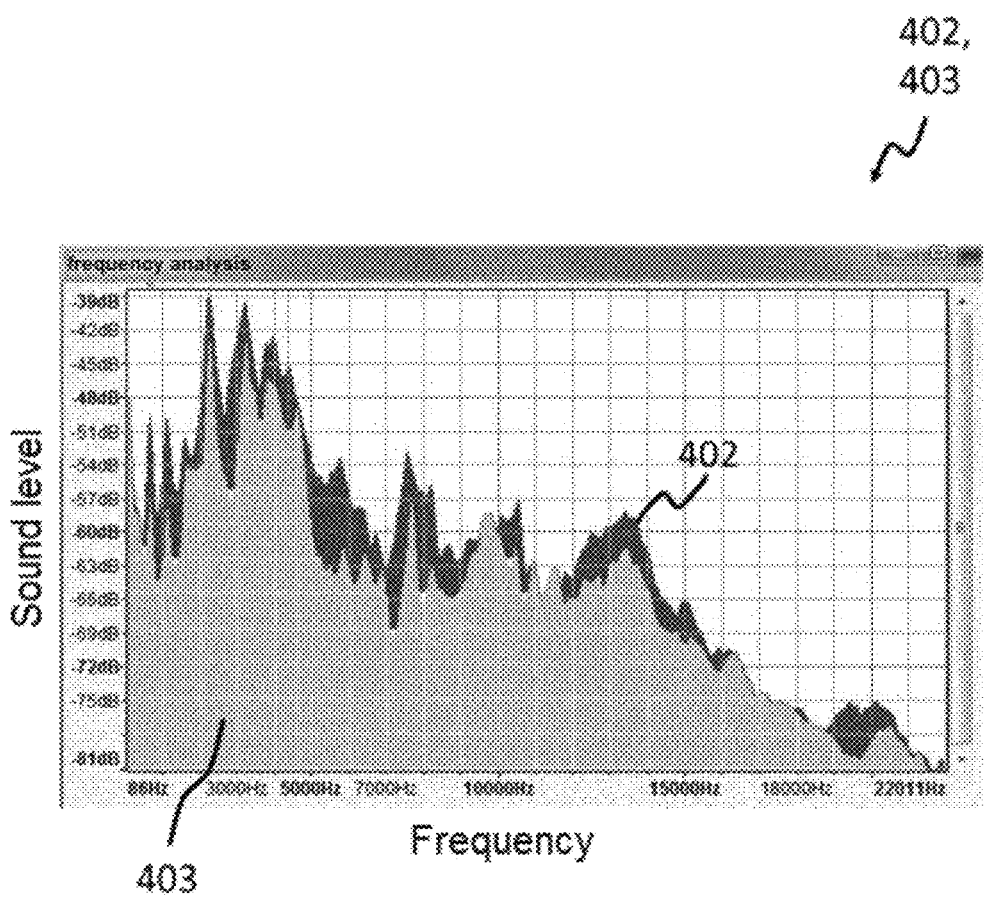

HAIR INFORMATION COLLECTION DEVICE, HAIR INFORMATION COLLECTION SYSTEM, AND METHOD FOR PROVIDING HAIR CONDITION INFORMATION

CROSS-REFERENCE TO RELATED APPLICATIONS

This application is a U.S. National-Stage entry under 35 U.S.C. § 371 based on International Application No. PCT/EP2017/083148, filed Dec. 15, 2017, which was published under PCT Article 21(2) and which claims priority to German Application No. 10 2016 225 964.4, filed Dec. 22, 2016, which are all hereby incorporated in their entirety by reference.

TECHNICAL FIELD

The present disclosure relates to a hair information collection device, a hair information collection system, and a method for providing information relating to the condition of a user's hair.

BACKGROUND

Users (also referred to as consumers) are often unaware of the degree to which their hair is damaged. This information can be important in order to be able to select the correct haircare product and/or hair dye (also referred to as hair colorant), i.e. one that is appropriate for the level of damage.

In particular, consumers are often lacking in product recommendations based on their external hair damage (damage to the hair cuticle (also referred to as the cuticula)), i.e. for example in respect of coarseness, frizz, splitting, etc.

An optimal product recommendation restores smoothness and shine to damaged hair (hair with damage to the cuticle), whereas an incorrect or improper cosmetic treatment that arises due to a lack of initial data may be time-consuming and costly.

A cosmetic method in which external hair damage can be analyzed under consideration of the cuticle hair surfaces by employing an acoustic emission system and a level of hair damage can be presented on the basis of noises and visual displays is provided in different exemplary embodiments.

Furthermore, the method can be used in different exemplary embodiments as the basis for a correct product recommendation, i.e. appropriate for the level of hair damage. For example, the user may receive an exact product recommendation for hair coloring, bleaching, permanent waving, hair nourishment and/or hair styling appropriate to the external level of hair damage.

SUMMARY

In different exemplary embodiments a user himself/herself may determine his/her external level of hair damage, for example without performing complex microscopy and/or without background knowledge provided by a suitable analysis. It may thus be made possible for the user to dispense with expert help when determining the condition of his/her hair.

In different exemplary embodiments the external hair damage can be determined by employing a device that has a sensor for detecting acoustic emissions, for example a microphone, for example by a contact microphone comb. The device is also referred to as a hair information collection device.

Herein the sensor for detecting acoustic emissions will also be referred to as a microphone for the sake of simplicity. Unless specified otherwise and suitable for the described function, however, the sensor for detecting acoustic emissions may also be an acceleration sensor (which may be suitable for detecting accelerations as a result of acoustic emissions in a certain frequency range) or the like.

Reference may be made herein to "the sensors", for example in respect of a data transmission between the sensors and a data processing device, or an array of sensors, etc. This is understood to mean that the sensors may comprise a totality of sensors and/or sensor circuits arranged in the hair information collection device, for example a totality of microphone(s), speed sensor circuit, possibly camera, etc., or, if clear from the context, some of the aforementioned sensors and/or sensor circuits.

The hair information collection device can be configured in different exemplary embodiments as a contact microphone comb. The contact microphone comb in different exemplary embodiments may comprise a substantially commercial hair comb, to which one or more externally mounted measurement systems for acoustic emissions (i.e. sound emissions; a contact microphone from the company Korg can be used as an exemplary measurement system for acoustic emissions) and/or measurement probes for acoustic emissions is/are attached.

The hair information collection device in different exemplary embodiments may comprise one or more measurement systems for acoustic emissions and/or probes which is/are incorporated fixedly in the hair information collection device, for example a hair comb.

In different exemplary embodiments signals of generated sound or vibration created as a user combs their hair can be recorded by employing the measurement systems for acoustic emissions.

The hair information collection device in different exemplary embodiments may comprise one or more measurement systems for acoustic emissions and/or probes, for example one or more contact microphones and/or an acceleration sensor. The hair information collection device in different exemplary embodiments may also comprise an internal or external amplifier for amplifying signals measured by the measurement system for acoustic emissions.

In different exemplary embodiments an analysis of hair damage can be provided by digitalizing information from a microphone (and at least one further sensor) and providing this data on a cloud platform. In different exemplary embodiments the microphone can be part of a hair information collection device.

The information can be provided following a processing for a comparison with examples already recorded (reference data). For the reference data a level of hair damage may be known, such that, as a result of the comparison, for example the level of hair damage of the most similar reference data can be provided, for example transmitted back, as a result in digital form.

By using various sensors, such as lenses, gyroscopes and accelerometers, it may be possible to determine the position of the hair information collection device, for example the position in the hand of a person, in order to determine a suitable form of cosmetic haircare (for example products, treatments) and to prevent unnecessary hair damage, for example hair loss.

The data transmission from the measurement system for acoustic emissions, for example the contact microphone and/or the acceleration sensor, to the amplifier can be realized in different exemplary embodiments by employing cables or via known wireless data standards (for example Bluetooth, WLAN, NFC, etc.).

The amplifier in different exemplary embodiments may comprise a signal processing and amplification system (also referred to as a signal conditioning system), which may be connected to a data acquisition system, which for its turn in part can be connected to a result memory, a correction processing means, and an output system.

Each of the aforementioned individual components (signal processing and amplification system, data acquisition system, result memory, correction processing means, output system) in different exemplary embodiments can be of commercial design or customized, and the measurement system for acoustic emissions can be combined arbitrarily with any one, all, or some of the above-described components.

In different exemplary embodiments the aforementioned components (or one or more thereof) can be provided, for example combined/integrated, in an electronic device, for example a mobile electronic device (also referred to as a mobile device), for example a smartphone or a tablet, or for example in another data processing device (for example a PC).

In different exemplary embodiments a (possibly further) external data processing device may also be used, for example by a cloud, for signal evaluation, for example as an extension of the signal evaluation. To this end, in different exemplary embodiments the signals detected by the sensors can be compared with signals stored in a database (also referred to as comparison signals, comparison data, reference signals or reference data). In different exemplary embodiments the external level of hair damage can be classified on this basis, for example by assigning levels of hair damage to the comparison signals and assigning to the measured hair the level of hair damage of the comparison signal most similar to the measured signal.

In different exemplary embodiments one or more of the aforementioned components (signal processing and amplification system, data acquisition system, result memory, correction processing means, output system) may be part of an electronic circuit device, which may be part of the hair information collection device, for example may be mounted in or on a device body of the hair information collection device.

In different exemplary embodiments, depending on which component is part of the electronic circuit device, a partially or fully processed signal can be provided by the hair information collection device, for example an amplified acoustic signal, a corrected acoustic signal, an acoustic signal processed under consideration of a determined speed, a level of hair damage determined by comparison of the acoustic signal with a database, a recommendation derived on this basis (for example likewise by the database), for example a recommendation for a cosmetic product and/or a cosmetic care treatment, etc.

The signal processing and amplification system can be connected to the measurement system for acoustic emissions in order to amplify a received noise, for example a received sound, and/or to manipulate a signal received via the acceleration sensor in order to provide a sound.

In different exemplary embodiments data received from one or more amplifier(s) can be transmitted to the data acquisition system. Alternatively, the data can also be transmitted directly from the measurement system for acoustic emissions to the data acquisition system.

In different exemplary embodiments the hair information collection device may also comprise a speed sensor circuit for detecting the speed of the hair information collection device. In different exemplary embodiments, for example in the event that the hair information collection device is formed in a number of parts and only one part (for example a device body), which comprises the sensors, is moved along the hair of the user, the speed sensor circuit can be designed such that it detects the speed of this part. In other words, the speed sensor circuit can be designed such that it detects the speed at which the part of the hair information collection device of which the movement along the hair of the user leads to an acoustic emission is moved or is moving.

The speed sensor circuit in different exemplary embodiments may comprise at least one sensor, which (for example in the case of just one sensor) considered alone or (for example in the case of a plurality of sensors) on the basis of sensor values from a plurality of sensors in combination enables a determination of the speed at which the speed sensor circuit is moved.

In different exemplary embodiments the speed sensor circuit may comprise for example an acceleration sensor as the at least one sensor, which acceleration sensor can be formed for example as a MEMS sensor or as a piezoelectric sensor.

In different exemplary embodiments the data detected by the speed sensor circuit can be transmitted to the data acquisition system.

In different exemplary embodiments a method for providing information regarding the hair of a user can use acoustic signals that are generated by contact between a hair information collection device and the hair surface and/or between a first hair surface and a second hair surface by a gliding over. Different vibration patterns that can be detected by a measurement system for acoustic emissions (for example a microphone) can thus be made accessible. The acoustic emissions, for example the different vibration patterns, can be recorded for example by employing a result memory, a correction processing feature, and an output system.

It has been found that the amplitude of an oscillation and of vibrations, and a frequency content of an acoustic signal or of waves (for example of vibrations) which are monitored as a function of time can be very sensitive to a change of hair-contact properties which are associated for example with a use of hair dyes, bleaching, hairstyling and haircare.

In different exemplary embodiments the signal, for example a wave, a time curve of a noise level and/or a frequency spectrum of an acoustic signal, can be associated or correlated with specific sensory properties. In different exemplary embodiments an analysis of the recorded signals may make it possible to characterize and to distinguish individual external levels of hair damage and/or to display and characterize the efficacy of haircare products.

In different exemplary embodiments for example acoustic signals in a frequency range of from approximately 86 Hz to approximately 22011 Hz, for example in a range of from approximately 1500 Hz to approximately 7000 Hz, and/or for example from approximately 7000 Hz to approximately 18000 Hz can be examined.

In different exemplary embodiments an acoustic signal, for example a (time-dependent) amplitude and/or a frequency of an acoustic signal, can be assessed integrated over an entire frequency range, for example one of the above-mentioned frequency ranges or a partial range thereof, for example as a level value integrated over the selected frequency range, and/or the acoustic signal can be subject to spectrally resolved analysis as a frequency spectrum, either for an entire frequency range, for example one of the above-mentioned frequency ranges, or a partial range thereof.

In the case of a spectrally resolved analysis a detected frequency spectrum in different exemplary embodiments can be compared with a plurality of reference frequency spectra. Here, the most similar reference frequency spectrum can be determined, for example in a manner known per se, for example by determining a squared deviation between the detected frequency spectrum and each of the reference frequency spectra, wherein the reference frequency spectrum with the smallest quadratic deviation may be the most similar frequency spectrum.

The reference frequency spectra in different exemplary embodiments can comprise empirically obtained (for example in a laboratory) frequency spectra for hair for which the level of damage may be known and can be assigned to the frequency spectrum, for example by employing a database. In different exemplary embodiments further information regarding the hair may also be provided which is used as a basis for the reference spectra, for example "hair bleached four times—high level of damage" or "untreated hair—no damage", and/or a progression of the condition of the hair, for example the level of damage to the hair, can be provided for the hair used for the determination of the reference spectra, for example a plurality of reference spectra each of which was recorded after another hair treatment stage, wherein the hair treatment may comprise a nourishing hair treatment and/or a damaging hair treatment. An agent (for example product and/or ingredient) which was used in a treatment may additionally have been detected by the database.

In different exemplary embodiments a user may also be provided with the additional information (for example taken from the database), for example the level of treatment to which his/her hair condition corresponds, and/or the way in which his/her hair condition is expected to progress if a specific treatment is followed, for example a specific agent is applied.

In different exemplary embodiments, for example with use of a cloud, the database may be generated by user data, alternatively to being generated in a laboratory. In different exemplary embodiments the database generated in a laboratory may be supplemented by user data, which can be provided by the cloud.

In different exemplary embodiments an acoustic signal, for example a (time-dependent) amplitude and/or a frequency of an acoustic signal, can be dependent on the speed at which the hair information collection device is moved along the hair of the user.

In different exemplary embodiments the speed at which the hair information collection device is moved along the hair of the user (referred to for the sake of simplicity as combing speed, even for cases in which the hair information collection device is not in the form of a comb) can be suitable for the method for providing information regarding the hair of a user if it lies within a range between more than 0 cm/s and approximately 30 cm/s, wherein a range of from approximately 5 cm/s to approximately 15 cm/s may be better suited.

In different exemplary embodiments the hair information collection device may be designed to determine the combing speed, for example by employing speed sensors as described herein elsewhere.

In different exemplary embodiments the determined speed can be used to provide the user with feedback as to whether he/she is combing his/her hair at a speed suitable for the method. For example, a signal sound and/or a signal light (for example red) and/or a display on a coupled display device can be provided if combing is performed at an excessively slow or an excessively high speed. In different exemplary embodiments the user may also be informed, for example by a signal light in another color (for example green) and/or by a display on the display device, that he/she is combing at the correct speed. In different exemplary embodiments the acoustic signal may be evaluated only if combing is performed at a suitable speed.

In different exemplary embodiments it may be possible to evaluate the acoustic signal at any combing speed (greater than zero).

In different exemplary embodiments the reference spectra or reference loudnesses that were generated at a comparable combing speed, for example at a combing speed not deviating by more than about 20%, for example not more than about 10%, from the determined combing speed, can be selected as comparison spectra or as comparison loudnesses from the database by the determined speed.

In different exemplary embodiments an influence of a combing speed on a spectrum and/or a loudness can be determined, for example by laboratory tests, and can be taken into consideration in a comparison of the detected frequency spectrum with the reference spectrum and/or the reference loudness. For example, a combing of the same hair with increasing combing speed may lead to a shift of the acoustic frequency spectrum towards higher frequencies or to an increase of its amplitude (and thus also to a higher loudness). Previously determined correction factors can thus be applied for any of the reference spectra not recorded at the same (or a similar) combing speed as the determined frequency spectrum (or vice versa the frequency spectrum can be adapted to the reference spectrum used for the comparison), such that a comparison of the determined frequency spectrum with that of the reference spectra of the database is made possible.

In different exemplary embodiments a loudness detected by the device for detecting the acoustic emission (for example the microphone) during the combing of the hair of the user may lie in a range from approximately −81 dB to approximately −10 dB, for example from approximately −81 dB to approximately −35 dB. Here, −81 dB corresponds to the lowest loudness which can still be detectable by the device for detecting the acoustic emission (for example the microphone). Since dB represents a logarithmic unit, −35 dB corresponds to a loudness which is greater by a factor of more than 10000 than the lowest loudness, and −10 dB corresponds to a loudness which is almost $10^7$ times louder than the lowest loudness, wherein however the high loudnesses, compared to loudnesses of ambient noises, may also still be comparatively quiet.

In different exemplary embodiments the hair information collection device can be provided as an accessory, for example a "clever accessory" (also referred to as "smart accessory") for a smartphone (or a similar device, such as a tablet, an iPod, or the like), which can be connected to the smartphone, for example plugged thereinto, whereby it can be made possible to utilize processing possibilities and/or sensors of the smartphone.

In different exemplary embodiments the hair information collection device can be provided as an independent device, which for example may comprise a separate device for transmitting data and therefore may be what is known as an "Internet-of-things (JOT)" device. The independent hair information collection device can transmit the recorded data (for example acoustic data and possibly speed data) for example by Bluetooth, Wi-Fi, NFC or the like, to an external data processing device, for example to a cloud.

In different exemplary embodiments the recorded data, as described herein elsewhere, can be analyzed by software algorithms, for example by comparing acoustic frequency spectra to reference spectra already recorded (or more generally acoustic data with reference data) in order to determine a level of hair damage.

In different exemplary embodiments, for example of the reference data provided by the cloud, these can be made available to a user at any moment in time in order to be used as reference data for comparison.

In different exemplary embodiments the data detected by the hair information collection device, for example an acoustic frequency spectrum and/or a loudness, and/or values and/or recommendations determined on the basis thereof can be stored, for example in a memory integrated in the hair information collection device and/or in the external data processing device, for example the cloud. The stored data can be stored such that it is possible at least for the user to identify this data as their own data. A comparison between hair information obtained for example at different moments in time (for example before and after a treatment) can thus be made possible.

In different exemplary embodiments data from sensors, such as a microphone, can be converted by employing the hair information collection device, possibly with the aid of an external data processing device. Services of a cloud can be utilized for a precise analysis and a comparison of the data (for example a comparison of the data with reference data).

The hair information collection device may use a combination of sensors, for example at least one gyroscope and/or one acceleration sensor, in order to determine the position of the hair information collection device in space. In addition, the speed of the hair information collection device can be determined on the basis of a change over time of the position in space and/or the acceleration.

In different exemplary embodiments, for example in the case that the hair information collection device is or comprises an accessory part which for example may be intended for connection to a smartphone, for example an iPhone, the (integrated) sensors of the smartphone can be used as the speed sensors.

In different exemplary embodiments the hair information collection device and/or the hair information collection system may have a connection for the transmission of data, for example between a smartphone/tablet, which can be part of the hair information collection system, and a cloud, and/or between the hair information collection device and a smartphone/tablet, and/or between a hair information collection device and a cloud.

In different exemplary embodiments a known data transmission standard can be used for the data transmission, for example Bluetooth, Wi-Fi, NFC or the like. In different exemplary embodiments the hair information collection device or the hair information collection system can comprise a corresponding data transmission device for transmitting and/or receiving data.

In different exemplary embodiments data collected by the hair information collection device (i.e. the determined at least one sensor value and/or data and/or recommendations determined on the basis thereof) can be provided.

In different exemplary embodiments merely the determined sensor values can be transmitted to and displayed on a display device (for example a smartphone or the like).

In different exemplary embodiments the sensor values can be examined (for example analyzed and/or evaluated) differently. Here, the examination in different exemplary embodiments can relate to currently collected data (a current cosmetic condition (also referred to as cosmetic state)) and/or to a change over time of the data (of the cosmetic state).

In different exemplary embodiments the analysis can be performed by the hair information collection device itself, for example by the circuit device, and an analysis result can be transmitted to a display device for providing the analysis result, for example to a display, a loudspeaker, a smartphone or the like.

In different exemplary embodiments, the data can be transmitted, for example preferably, to an external data processing device (also referred to as external platform), for example to a smartphone with app, to a cloud, etc. Following the data transmission to the external data processing device, the examination of the data by the processing device can be performed, for example in order to determine a recommendation.

In different exemplary embodiments the data evaluation may be the basis of a recommendation, for example a product and/or method recommendation, for example the recommendation may comprise what are known as DOs (instructing recommendations) and DON'Ts (warning recommendations), for example (as an example of a DO) "use shampoo X and style your hair using mousse Y" or (as an example of a DON'T) "do not use basic perms".

In different exemplary embodiments the consumer can be provided with current, personal data regarding the cosmetic state of their hair, for example a level of damage to their hair surface (the hair cuticle).

In different exemplary embodiments the possibility of determining the cosmetic (hair damage) state of their hair themself may relieve the consumer of the need to visit a specialist (for example hairdresser).

In different exemplary embodiments a coordination of the cosmetic treatment with individualized consumer data may enable an iterative cosmetic treatment cycle, may improve the result of the cosmetic treatment, and/or may increase the motivation of the user to continue the treatment.

In different exemplary embodiments information regarding the condition of the hair (also referred to as the hair state) can be provided to a user and can be used further to determine an individual recommendation coordinated with the hair condition of the user, for example a product recommendation (for example for a haircare and/or a hairstyling product) and/or a care recommendation, for example a care recommendation relating to the hair of the user.

In different exemplary embodiments the recommendation can be determined directly by the hair information collection device, i.e. the electronic circuit device can be designed to determine the recommendation itself (also referred to as "directly"). For example, the electronic circuit device may be or may comprise a data processing device, for example it can be equipped with a memory and a processor, for example a microprocessor, which can be designed, for example by a programming, to receive the sensor data and either to provide it directly to the user or to use it to provide the recommendation. For example, the sensor data can be compared with a database, which for example may have been obtained empirically. A plurality of sensor data items, for example a plurality of microphone data items, which for example can be related to a speed in each case, can be assigned in the database to recommendations.

In different exemplary embodiments the electronic circuit device can be designed to determine the recommendation, for example product or treatment recommendation, indirectly. For example, the electronic circuit device (for example additionally to a memory and a processor, for example a microprocessor) can be equipped with a data transmission device, which can be designed to transmit the sensor data received from the electronic circuit device to an external data processing device, for example to a computer, for example a cloud, by which, for example as described above for the determination of the recommendation by the electronic circuit device, the recommendation can be determined, in order to provide the recommendation, for example by transmission to a recommendation and/or by transmission of the recommendation back to the electronic circuit device (for example by the data transmission device). In different exemplary embodiments the data transmission can be realized in a number of steps, for example by firstly transmitting the sensor data from the circuit device to the display device (for example smartphone, tablet, or the like), and by the display device transmitting the sensor data to the external data processing device (for example the cloud).

In different exemplary embodiments the provision of the recommendation to the user may comprise a provision by a transmission of the recommendation to a display device and display of the recommendation.

The transmission can be realized in different exemplary embodiments by employing a wireless transmission device. The wireless transmission device for example may be part of the electronic circuit device. The wireless transmission device in different exemplary embodiments may comprise a chip or tag, which enables the wireless data transmission, for example by Bluetooth WLAN, ZigBee, NFC, Wibree, Threald, WiMAX or the like.

In different exemplary embodiments the display device may comprise a computer screen, smartphone, a tablet, an iPad, laptop or the like.

In different exemplary embodiments a hair information collection system can be formed by a hair information collection device and the display device.

As a variant of the above examples, other combinations of two or more recommendations can be provided by the display device in different exemplary embodiments.

In different exemplary embodiments the hair information collection device may also comprise a camera for recording at least one digital image of the hair of the user. The image recorded by the camera can be provided to the electronic circuit device. The image can be used in different exemplary embodiments for example directly (for example by the electronic circuit device) or indirectly (for example by external data processing device), for example by comparison with reference data, in order to determine hair condition information, for example a visual level of damage. The hair condition information determined by the camera can be included in the determination of a recommendation, for example a product or treatment recommendation.

In different exemplary embodiments the camera may also be used in a determination of a speed at which the device body (in or on which the camera may be arranged) is moved along the hair of the user. For example, a plurality of images of the hair can be recorded by the camera and make it possible to determine a traveled path along the hair. The speed can thus be determined with inclusion of the times at which the digital images are recorded. The determined speed, as described herein elsewhere, can be evaluated in conjunction with the determined acoustic signals in order to determine hair condition (for example hair damage) information.

In different exemplary embodiments a hair information collection device for providing information relating to the hair of the user is provided. The hair information collection device may comprise a device body having at least a first region and a second region, which are designed such that the hair of the user is movable between the first region and the second region whilst in contact with the first region and the second region, at least one microphone arranged in or on the device body for detecting a noise during movement of the hair between the first region and the second region, a speed sensor circuit which is arranged in or on the device body and which comprises at least one sensor for determining a value representing the speed of the device body, and an electronic circuit device arranged in or on the device body, wherein the electronic circuit device can be coupled to the at least one microphone and the speed sensor circuit in order to receive the detected noise and the speed of the device body, and wherein the electronic circuit device can be designed to provide the user with information regarding his/her hair on the basis of the received detected noise and the speed of the device body.

In different exemplary embodiments the device body can be formed as a comb or as a brush, and the first region and the second region can comprise two adjacent comb teeth or two adjacent bristles of the brush.

In different exemplary embodiments the electronic circuit device can be designed to determine hair condition information on the basis of the detected noise and the speed of the device body and to provide said information to the user.

In different exemplary embodiments the electronic circuit device can be designed to determine a recommendation on the basis of the detected noise and the speed of the device body and to provide said recommendation to the user.

In different exemplary embodiments the recommendation may comprise at least one of a haircare product recommendation, a hairstyling product recommendation, and a hair treatment recommendation.

In different exemplary embodiments the at least one microphone may comprise a plurality of microphones.

In different exemplary embodiments the at least one microphone may be sealed in the device body.

In different exemplary embodiments the electronic circuit device may comprise a wireless data exchange device.

In different exemplary embodiments the hair information collection device may also comprise a camera for recording a digital image of the hair of the user.

In different exemplary embodiments a hair information collection system is provided. The hair information collection system may comprise a hair information collection device according to different exemplary embodiments, and a display device, wherein the at least one hair information collection device can be designed to transmit to the display device the information regarding the hair of the user by the data exchange device.

In different exemplary embodiments the display device may comprise a computer screen, smartphone, a tablet, an iPad, or laptop.

In different exemplary embodiments a hair information collection system for providing information relating to the hair of the user is provided.

The hair information collection system may comprise a device body having at least a first region and a second region, which are designed such that the hair of the user is movable between the first region and the second region whilst in contact with the first region and the second region, at least one microphone arranged in or on the device body for detecting a noise during movement of the hair between the first region and the second region, an electronic circuit device arranged in or on the device body, a data processing device with a housing, a speed sensor circuit which is arranged in the housing of the data processing device and which comprises at least one sensor for determining a value representing the speed of the data processing device, wherein the device body is designed to be fixedly connected to the data processing device so that the speed of the data processing device is the same as the speed of the device body, wherein the electronic circuit device is coupled to the at least one microphone in order to receive the detected noise, wherein the data processing device is coupled to the speed sensor circuit in order to receive the speed of the device body, and wherein the data processing device is designed to provide the user with information regarding his/her hair on the basis of the received detected noise and the speed of the device body.

In different exemplary embodiments the data processing device may comprise a smartphone or tablet.

In different exemplary embodiments a method for providing information relating to the hair of the user is provided. The method may comprise the steps of moving a hair information collection device according to different exemplary embodiments in such a way that the hair of the user moves between the first region and the second region whilst in contact with the first region and the second region, detecting a noise by the at least one microphone and the speed of the device body by the speed sensor circuit during the movement of the device body, and providing the user with information regarding his/her hair on the basis of the detected noise and the speed of the device body.

In different exemplary embodiments the method may also comprise a step of determining at least one piece of hair condition information on the basis of the detected noise and the speed of the device body.

In different exemplary embodiments the method may also comprise a step of determining at least one recommendation on the basis of the detected noise and the speed of the device body.

In different exemplary embodiments the recommendation may comprise at least one of a haircare product recommendation, a hairstyling product recommendation, and a hair treatment recommendation.

In different exemplary embodiments the method may also comprise a step of transmitting the detected noise and the detected speed to an external data processing device, and a step of receiving the information provided by the external data processing device, wherein the at least one piece of hair condition information can be determined on the basis of the detected noise and the speed by the external data processing device.

In different exemplary embodiments the external data processing device may comprise or may be a cloud.

BRIEF DESCRIPTION OF THE DRAWINGS

The present disclosure will hereinafter be described in conjunction with the following drawing figures, wherein like numerals denote like elements, and:

FIG. 4A and FIG. 4B show exemplary measured values of a microphone of a hair information collection device in accordance with different exemplary embodiments.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Reference is made in the following detailed description to the accompanying drawings, which form part of the present application and in which specific embodiments in which the present disclosure can be carried out are shown by way of illustration. In this regard, directional terminology such as "top", "bottom", "in front of", "behind", "front", "rear", etc. is used with reference to the orientation of the described figure(s). Since components of embodiments can be positioned in a number of different orientations, the directional terminology is used by way of illustration and is in no way limiting. It goes without saying that other embodiments can be used, and structural or logical modifications can be made, without departing from the scope of protection of the present disclosure. It goes without saying that the features of the different exemplary embodiments described herein can be combined with one another, unless specifically stated otherwise. The following detailed description therefore is not intended to be limiting, and the scope of protection of the present disclosure is defined by the accompanying claims.

Figure 1:
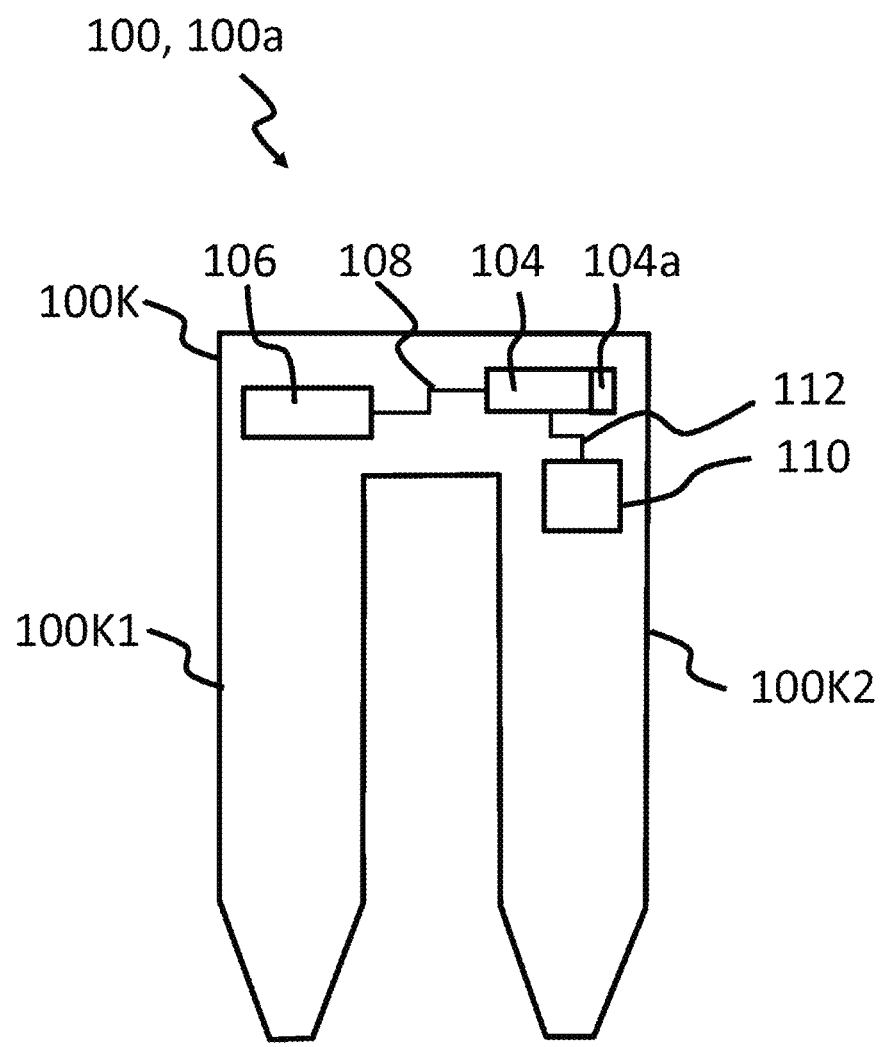
FIG. 1 shows a schematic depiction of a hair information collection device in accordance with different exemplary embodiments.
Figure 2A:
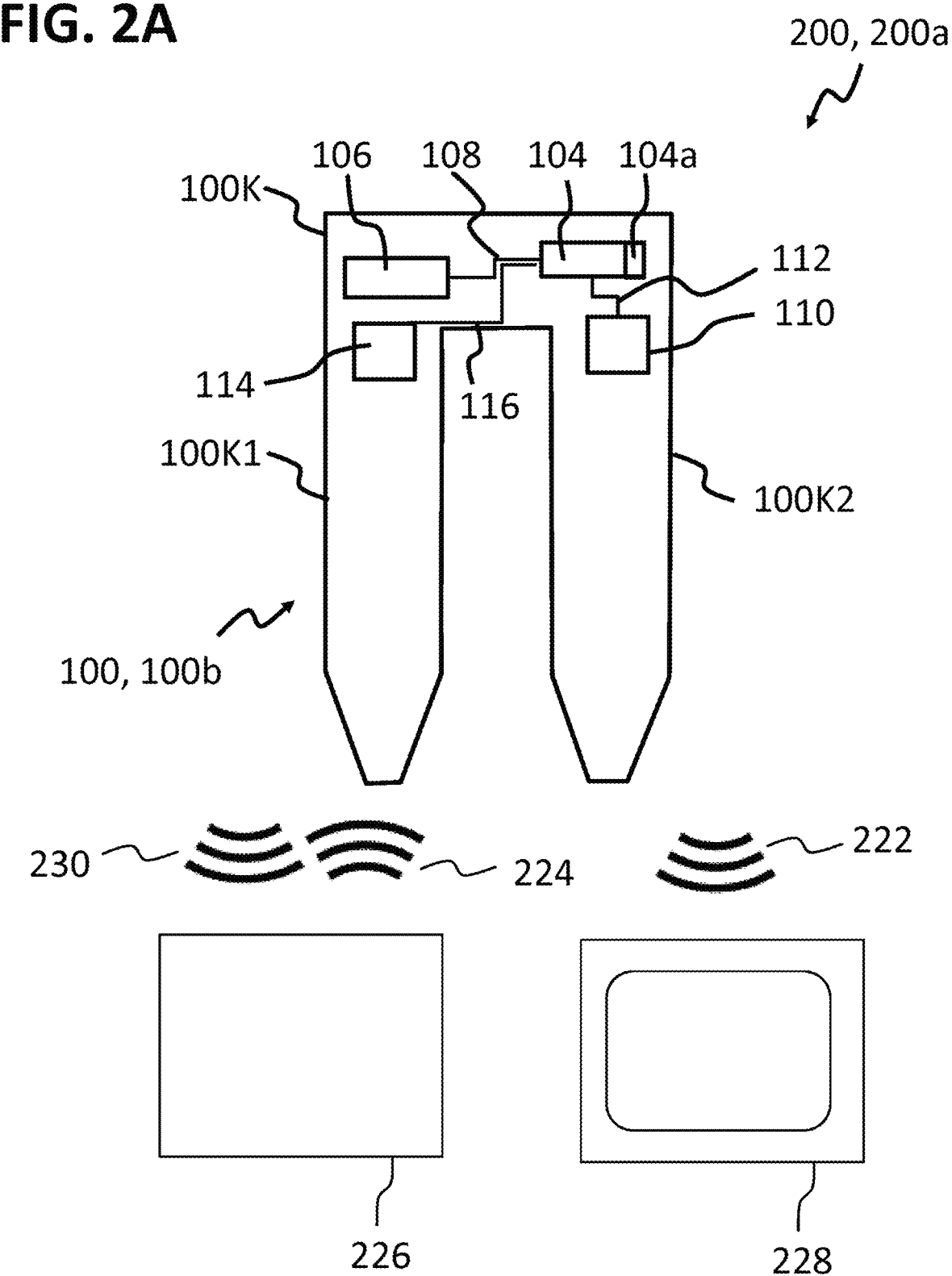
FIG. 2A shows a schematic depiction of a hair information collection system in accordance with different exemplary embodiments in conjunction with an external data processing device.
Figure 2B:
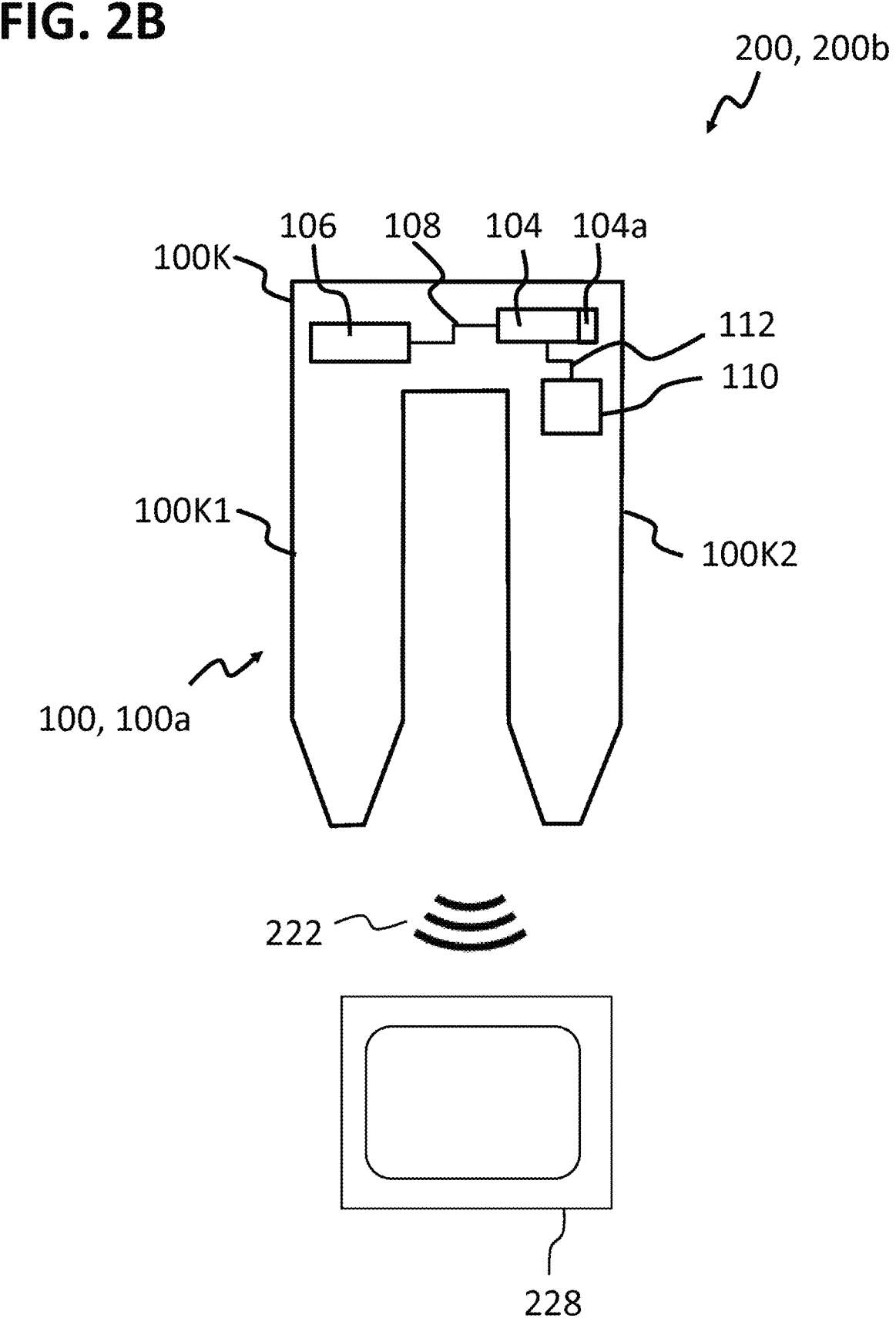
FIG. 2B shows a schematic depiction of a hair information collection system in accordance with different exemplary embodiments.
Figure 3A:
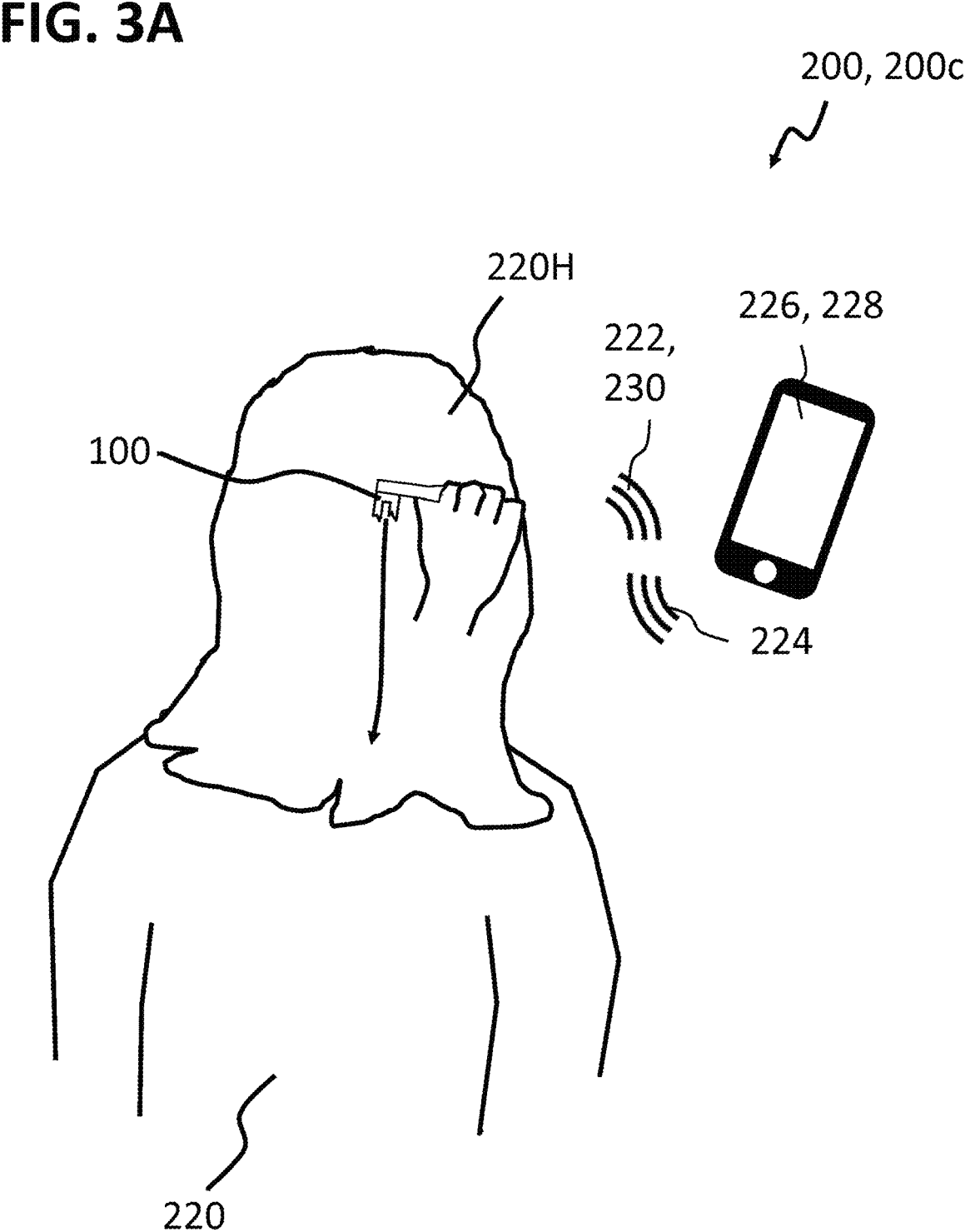
FIG. 3A shows a schematic depiction of an application of a hair information collection system in accordance with different exemplary embodiments.
Figure 3B:
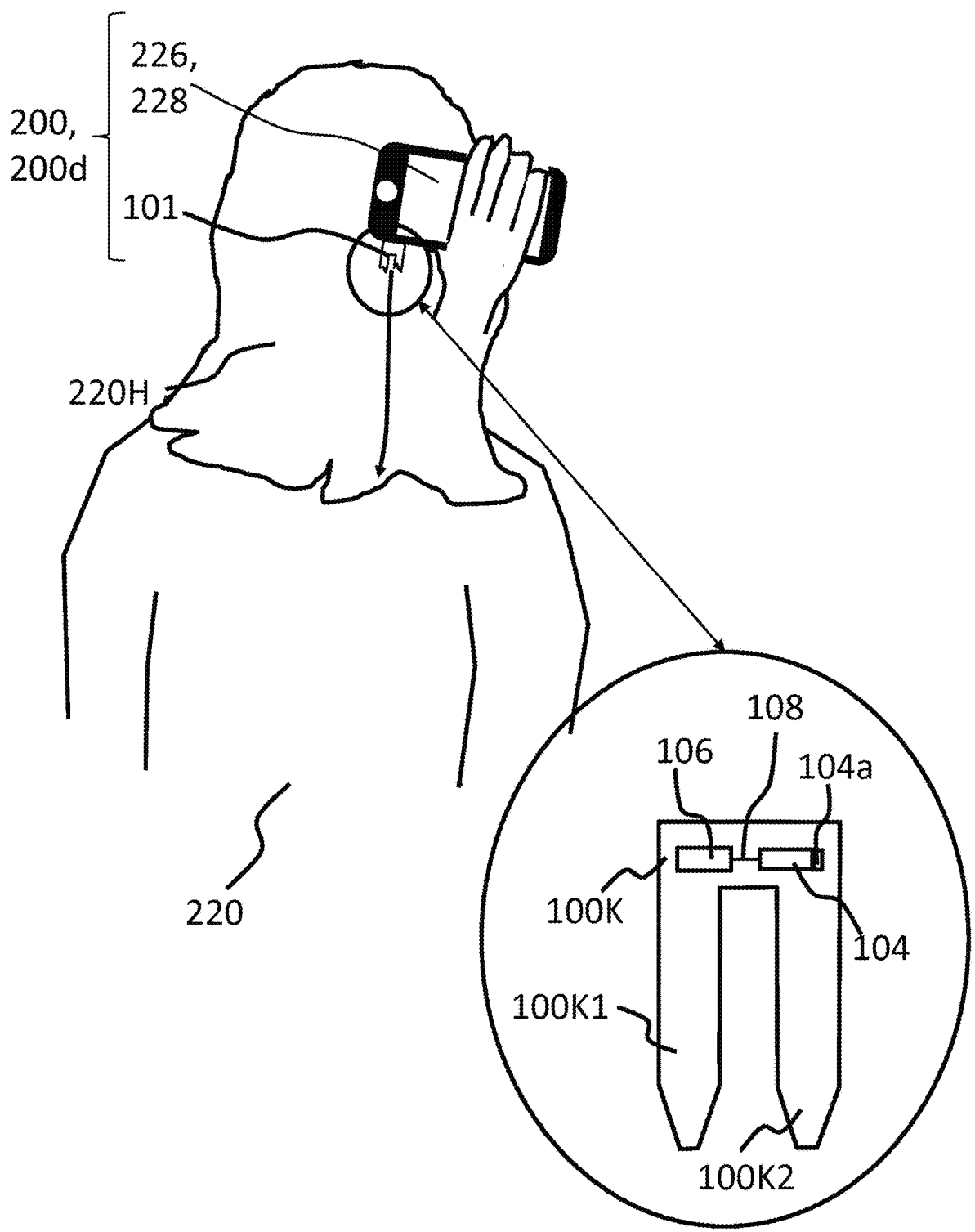
FIG. 3B shows a schematic depiction of an application of a hair information collection system in accordance with different exemplary embodiments.

FIG. 1 shows a schematic depiction of a hair information collection device 100, 100a in accordance with different exemplary embodiments, FIG. 2A shows a schematic depiction of a hair information collection system 200, 200a in accordance with different exemplary embodiments in conjunction with an external data processing device, FIG. 2B shows a schematic depiction of a hair information collection system 200, 200b in accordance with different exemplary embodiments, FIG. 3A shows a schematic depiction of an application of a hair information collection system 200, 200c in accordance with different exemplary embodiments, and FIG. 3B shows a schematic depiction of an application of a hair information collection system 200, 200d in accordance with different exemplary embodiments.

A hair information collection device 100 is provided in different exemplary embodiments (different exemplary embodiments are denoted as 100a and 100b).

In different exemplary embodiments the hair information collection device 100 may comprise a device body 100K.

The device body 100K can be formed from a solid material, for example plastic or metal, or can comprise a material of this kind. For example, the device body 100K can be formed from a material or can comprise a material that is usually used for a comb, brush, or a straightening iron.

The device body 100K in different exemplary embodiments can have at least a first region 100K1 and a second region 100K2, which can be designed such that the hair 220H of a user is movable between the first region 100K1 and the second region 100K2 whilst in contact with the first region 100K1 and the second region 100K2, for example such that the hair slides along the first region 100K1 and the second region 100K2.

The hair information collection device 100 (or at least the device body 100K) can be intended, in accordance with different exemplary embodiments, to be guided along the hair 220H of the user 220 in a combing movement, more specifically in such a way that whilst the combing movement is being performed the hair 220H of the user 220 moves between the first region 100K1 and the second region 100K2, wherein it is in contact with the first region 100K1 and the second region 100K2.

This is understood to mean that the hair 220H is in contact with the first region 100K1 and the second region 100K2, that a plurality of hairs 220H, for example a strand or a cluster, are disposed between the first region 100K1 and the second region 100K2, a part of the plurality of hairs 220H is in contact with the first region 100K1, and a part of the plurality of pairs 220H is in contact with the second region 100K2. In various exemplary embodiments one, a plurality, or all of the hairs 220 of the plurality of pairs 220H can be in contact with both the first region 100K1 and the second region 100K2.

In various exemplary embodiments the hair information collection device 100 can be formed as a comb or comb-like device. The first region 100K1 and the second region 100K2 can then be formed for example as (adjacent) comb teeth. In various exemplary embodiments, in the case of a comb having more than two teeth, each gap between adjacent teeth can be considered to be a gap between a first region 100K1 and a second region 100K2, i.e. the comb can be understood such that it comprises a plurality of adjacent first and second regions, between which in each case there is arranged a gap, in which the hair 220H of the user 220 is moved such that it slides through against the two comb teeth. This can occur during a conventional combing process.

A combing process of this kind is shown schematically in FIG. 3A and FIG. 3B. In order to illustrate that, during a movement (indicated by an arrow) of the hair information collection device 100 along the hair 220H of the user 220, some of the hair 220H is disposed between the comb teeth which form the first region 100K1 and the second region 100K2, the hair information collection device 100 is shown in FIG. 3A and FIG. 3B such that substantially only one connection piece can be seen, which connects the first region 100K1 and the second region 100K2.

In different exemplary embodiments it may be necessary (for a comparison with reference data, as described herein elsewhere) to comb the hair 220H of the user 220 from the hair root in the direction of the hair tip.

Herein, a process in which the hair 220H is moved between the first region 100K1 and the second region 100K2 can be referred to as "combing", even if the hair information collection device 100 is not designed in the form of the comb.

In various exemplary embodiments the hair information collection device 100 can be formed for example as a brush or with a brush-like design, for example not with teeth arranged in one direction, as is the case in a comb, but with bristles arranged along two directions, or can be formed as a straightening iron or with a design similar to a straightening iron, i.e. with mutually opposed surfaces which are designed to press the hair 220H flat between them.

In different exemplary embodiments the hair information collection device 100 can comprise at least one sensor 106, arranged in or on the device body, for detecting acoustic emissions, for example a microphone 106 and/or an acceleration sensor 106 (which can be suitable for detecting accelerations as a result of acoustic emissions in a certain frequency range), or the like. As described above, the sensor for detecting acoustic emissions 106 can be referred to more simply as a microphone 106.

In various exemplary embodiments the microphone 106 can be designed to detect a noise during movement of the hair 220H between the first region 100K1 and the second region 100K2, for example during the combing process. In various exemplary embodiments the microphone 106 can be arranged in or on the device body such that it is suitable for detecting noises that can be generated during the combing by the hairs 220H sliding against the first region 100K1 and/or the second region 100K2 and possibly by a sliding of the hairs 220H against one another.

In different exemplary embodiments the microphone 106 can be arranged on the device body 100K such that a transmission of the combing noises to the at least one microphone 106 is made possible, for example is optimized. The at least one microphone 106 can be arranged for example in at least one of the comb teeth 100K1 or 100K2.

In different exemplary embodiments the microphone 106 can be incorporated in the device body 100K, for example incorporated therein in a sealed manner.

The hair information collection device can thus be made insensitive to moisture and dirt. For example, as a result of the sealed arrangement, the hair information collection device can be cleaned without damaging the microphone 106 or another device. The microphone 106 for example can be molded during an injection molding of the device body 100K.

In different exemplary embodiments the hair information collection device 100 can comprise a speed sensor circuit 110 arranged in or on the device body 100K, which circuit can comprise at least one sensor. The speed sensor circuit can be designed to determine a value representing a speed of the device body 100K. The speed sensor circuit 110 can be realized as described above in different exemplary embodiments. For example, the at least one sensor for determining the speed can comprise an acceleration sensor and/or a gyroscope and/or a camera, and/or any other conventional suitable device which is suitable for determining the speed of the device body. In order to determine the speed, time information can be taken into consideration in addition to the particular sensor signal. The value representing a speed of the device body 100K can be a speed value, a value proportional to the speed, a speed classification (for example suitable/unsuitable or too slow/suitable/too high, or a classification with more than three classes), or any other value representing speed that allows a selection of suitable reference values/spectra for the measured microphone data, for example a selection from reference values/spectra stored in a database.

In different exemplary embodiments the hair information collection device may comprise an electronic circuit device 104 arranged in or on the device body 100K.

The electronic circuit device 104 can be coupled in different exemplary embodiments to the at least one microphone 106, for example by a connection 108, in order to receive the detected sound. If a plurality of microphones 106 are provided, the circuit device 104 may have a separate coupling to each of the microphones 106. The coupling in different exemplary embodiments can comprise or be an electrically conductive connection, a (glass) fiber connection and/or a wireless connection. The electronic circuit device 104 can be designed to receive the at least one sensor value from the at least one sensor 106.

A signal-to-noise ratio can be improved by using a plurality of microphones.

The electronic circuit device 104 can be coupled in different exemplary embodiments to the speed sensor circuit 110, for example by a connection 112, in order to receive the speed of the device body 100K.

In different exemplary embodiments the electronic circuit device can be designed to provide the user 220 with information regarding his/her hair 220H on the basis of the received detected noise and the speed of the device body 100K.

Figure 4A:
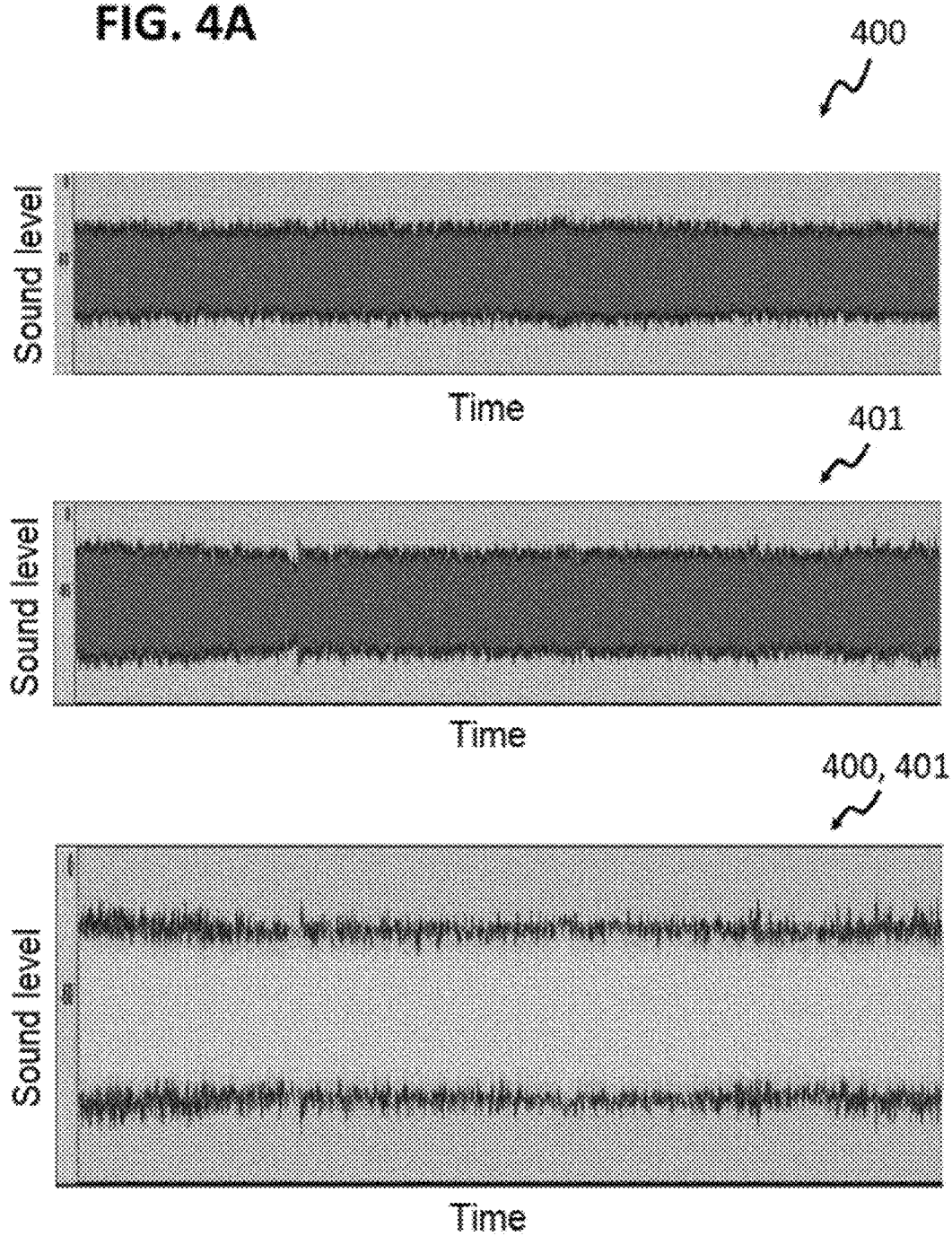

Furthermore, the electronic circuit device 104 can be designed in different exemplary embodiments to provide the user 220 with the received at least one sensor value, for example in the form of a substantially unprocessed signal, for example in the form of a sound level that is variable over time (in this regard see FIG. 4A as an example), and/or as processed signal, for example an acoustic frequency spectrum (in this regard see FIG. 4B as an example).

In different exemplary embodiments the electronic circuit device 104 may be or may comprise a data processing device, for example it can be equipped with a memory and a processor, for example a microprocessor, which can be designed, for example by a programming, to receive the data from the microphone 106 and either to provide it directly to the user 220 or to use it to provide the recommendation.

The electronic circuit device 104 can be designed in different exemplary embodiments to determine at least one recommendation on the basis of the data received from the microphone 106 and to provide said recommendation to the user 220.

In different exemplary embodiments the speed sensor circuit 110 and the circuit device 104 can form an integrated circuit device (not shown).

In different exemplary embodiments the hair information collection device, for example as shown in FIG. 2A on the basis of the hair information collection device 100c, may also comprise a camera 114. The camera 114 can be coupled to the electronic circuit device 104 by a connection 116. The camera 114, as described above, can be used to determine the level of damage of the hair and/or to determine a speed. In the case that the camera 114, amongst other things, is also used at least to determine the speed, the camera 114 in different exemplary embodiments can also be connected to the speed sensor circuit 110 by a connection (not shown).

As is shown in the schematic illustrations of an application of hair information collection systems 200, 200c, 200d according to different exemplary embodiments, head hair 220H of a user 220 can be combed by the hair information collection device (i.e. the hair 220H can be moved between the first region 100K1 and the second region 100K2 whilst in contact with the first region 100K1 and the second region 100K2).

Acoustic signals generated as a result of the combing can be detected by employing the at least one microphone 106 and provided.

FIG. 4A and FIG. 4B show exemplary measured values of the microphone 106 of a hair information collection device 100, 101 in accordance with different exemplary embodiments.

In FIG. 4A a time-dependent sound level measured by the microphone 106, detected during the combing of hair having extremely little external hair damage is shown in the upper illustration 400, and a time-dependent sound level detected during the combing of very heavily damaged hair is shown in the middle illustration 401.

As is particularly clear on the basis of a superimposition of the two signals (shown in the lower illustration of FIG. 4A), the sound level of the combing of the damaged hair has a high amplitude, and therefore a higher loudness.

An examination of this kind of the loudness of the signal, for example for predefined frequency ranges, can be used to determine a (external) level of hair damage to the hair 220H of the user 220.

The following table shows an exemplary database entry which can be used to compare a determined loudness with loudnesses provided in the database. Here, it can be ensured by a combing speed determined by the speed sensor circuit 110 that a comparable speed was used when determining the reference loudnesses.

| Frequency range | Loudness | Level of hair damage |
| --- | --- | --- |
| 1500-7000 Hz | >−43 dB | very low |
| 1500-7000 Hz | >−42 dB | low |
| 1500-7000 Hz | >−41 dB | medium |
| 1500-7000 Hz | >−40 dB | severe |
| 1500-7000 Hz | >−39 dB | very severe |

In FIG. 4B frequency spectra of the detected noises from FIG. 4A are shown (illustration 402: very little external damage; illustration 403: very severe external damage, page 2: superimposition of 402 and 403).

As can be seen in particular on the basis of the superimposition, the damaged hair 220H during combing leads to louder acoustic emissions at almost any frequency.

In different exemplary embodiments the entire spectral range can be considered for the determination of a reference spectrum best matching the detected spectrum.

In different exemplary embodiments particularly suitable frequency ranges which enable simple differentiation of the degrees of damage can be identified by an examination of the reference spectra, for example ranges in which the frequency spectra of only slightly damaged hair and severely damaged hair are strongly differentiated, in the example from FIG. 4B for example a range between approximately 5000 Hz and approximately 9000 Hz.

Similarly to the exemplary table for loudnesses, degrees of damage can be assigned to the reference spectra which can be used for comparison. The hair of the user 220 can thus be assigned to the degree of damage corresponding to the most similar reference spectrum.

In different exemplary embodiments it is therefore possible to determine the external level of hair damage by employing the frequency analysis.

In different exemplary embodiments a database can also provide a product recommendation on the basis of the level of hair damage.

As shown in the table below, at least one product recommendation for example (also a styling or other hair treatment recommendation) can be assigned to the level of hair damage in the database.

| Level of hair damage | Product recommendation |
|---|---|
| very low | Product with very small nourishing component |
| low | Product with small nourishing component |
| medium | Product with medium nourishing component |
| severe | Product with high nourishing component |
| very severe | Product with very high nourishing component |

The detected (measured) sensor values, as described above, can be evaluated either directly in the hair information collection device 100, for example by the electronic circuit device 104, or can be evaluated indirectly by being transmitted to an external data processing device 226 and evaluated there, for example as described above. Here, the sensor data or parts of the sensor data can be evaluated in different exemplary embodiments by a comparison with (for example empirically obtained) database entries.

In different exemplary embodiments a determined level of hair damage can be included when determining a recommendation, for example a product or treatment recommendation.

In different exemplary embodiments the hair information collection device 100 in conjunction with a display device 228 and/or an external data processing device 226 can be considered to be a hair information collection system 200. In FIG. 2A and FIG. 2B exemplary hair information collection systems 200 are shown.

As described above, the electronic circuit device 104 can be designed in various exemplary embodiments to determine at least one piece of information and/or one recommendation on the basis of the received at least one sensor value (the noise and the speed detected by the microphone) and to provide these/this to a user by, as illustrated for example in FIG. 2B, determining the information and/or recommendation itself (directly), for example as described above, for example by comparison with reference spectra, values, value ranges and/or data in databases stored in a memory of the electronic circuit device 104, wherein the reference values, value ranges and/or data in databases can be assigned in each case to at least one recommendation.

As described above, the electronic circuit device 104 can be designed in various exemplary embodiments to determine at least one piece of information and/or one recommendation on the basis of the received at least one sensor value (the noise and the speed detected by the microphone) and to provide these/this to a user by, as illustrated for example in FIG. 2A, determining the recommendation indirectly, for example as described above, for example by transmitting (illustrated as a transmission signal 230) the at least one sensor value to an external data processing device 226, for example an external computer, for example a cloud, comparing same with reference spectra, values, value ranges and/or data in a database stored in a memory of the external data processing device 226, wherein the reference values, value ranges and/or data in the database can be assigned in each case to at least one recommendation. The hair information collection device 100 can be designed to receive the recommendation determined by the external data processing device 226, i.e. the determined recommendation can be transmitted to the hair information collection device 100 (illustrated as a transmission signal 224).

In different exemplary embodiments a hair information collection system 200 can be provided, as shown by way of example in 2A, FIG. 2B, FIG. 3A and FIG. 3B.

The hair information collection system, as shown in FIGS. 2A, 2B and 3A, can comprise, in different exemplary embodiments, a hair information collection device 100 according to different exemplary embodiments and a display device 228.

The hair information collection system, as shown in FIG. 3B, can comprise, in different exemplary embodiments, a hair information collection device 101 and a display device 228. The hair information collection device 101 can differ from the hair information collection device 100 in that it does not have a separate speed sensor circuit 110, and instead is designed to be fixedly connected, for example by a holder, a plug, or the like, to the display device 228, which is integrated with the data processing device 226, for example in the form of a smartphone, tablet, or a similar device. It can thus be made possible to use, instead of the speed sensor circuit 110, a sensor integrated in the combined display device/data processing device 228/226 in order to determine the speed of the device body 100K. By employing the fixed connection between the hair information collection device 101 and the display device/data processing device 228/226, it can be ensured that the speed of the display device/data processing device 228/226 corresponds to the speed of the device body 100K.

In order to transmit the at least one sensor value and/or the at least one recommendation to the display device 228 and/or in order to transmit the at least one sensor value to the external data processing device 226 and/or in order to receive the at least one recommendation from the external data processing device 226, the hair information collection device 100/101 can be equipped with a transmission device 104a for wireless data transmission (via transmission signal 230 and/or 222), for example with a chip or tag, which enables wireless data transmission, for example by employing Bluetooth, WLAN, ZigBee, NFC, Wibree, Threald, WiMAX or the like. In different exemplary embodiments the transmission device 104a can be part of the electronic circuit device 104.

As shown in FIG. 3A and FIG. 3B, the display device 228 in different exemplary embodiments can form an integrated unit with the data processing device 226, for example in the form of a smartphone, tablet, laptop, iPad, or the like.

In different exemplary embodiments the hair information collection device can comprise an integrated power supply (not shown), for example rechargeable batteries or the like, which can provide an operating voltage for the electronic circuit device 104, the transmission device 104a, and the at least one sensor 106. The power supply can be designed to be exchangeable in different exemplary embodiments. In different exemplary embodiments the power supply can be arranged in the hair information collection device 100 in a sealed (for example watertight) manner, for example in a molded manner. In that case the power supply can be chargeable inductively, for example.

Figure 5:
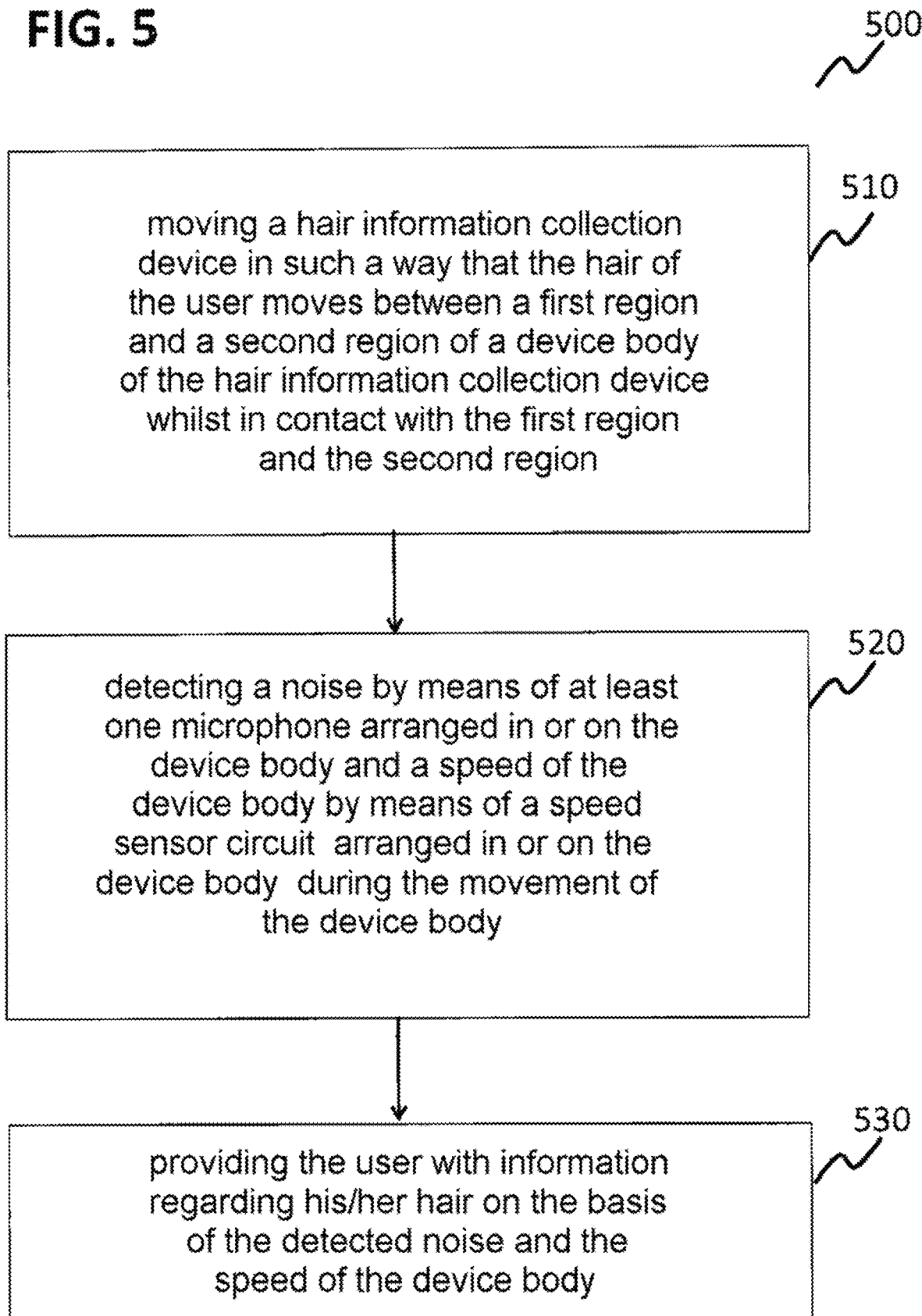
FIG. 5 shows a flow diagram of a method for providing hair condition information in accordance with different exemplary embodiments.

FIG. 5 shows a flow diagram 500 of a method for providing hair condition information in accordance with different exemplary embodiments.

In a method for providing hair condition information in accordance with different exemplary embodiments a hair information collection device in accordance with different exemplary embodiments and/or a hair information collection system in accordance with different exemplary embodiments can be used.

The method can comprise a step of moving a hair information collection device in such a way that the hair of the user moves between a first region and a second region of a device body of the hair information collection device whilst in contact with the first region and the second region (510), a step of detecting a noise by at least one microphone arranged in or on the device body and a speed of the device body by a speed sensor circuit arranged in or on the device body during the movement of the device body (in 520), and a step of providing the user with information regarding his/her hair on the basis of the detected noise and the speed of the device body (in 530).

A programming, for example a software, can be used in different exemplary embodiments for the above-described determinations. Here, any software that provides a functionality as described above can be used. In different exemplary embodiments, for example in the case that a smartphone, tablet or the like is used to carry out the method for providing hair condition information in accordance with different exemplary embodiments, the software can be provided in the form of an app.

In different exemplary embodiments a suitable haircare agent, hairstyling agent, a hair treatment recommendation or the like for example can be determined for the hair, for example by a comparison of the sensor values with provided reference values.

In different exemplary embodiments the circuit device and/or an external data processing device, for example a smartphone, tablet, laptop, smart mirror, an iPad, or the like integrated in the hair information collection device may be suitable for use when carrying out the method for providing hair condition information, for example in determination procedures, for example by comparison with a database/reference values or the like. In different exemplary embodiments the programming/software does not need to be provided on the smartphone, tablet, laptop, etc. For example, it may be sufficient if the circuit device and/or the smartphone, or the like integrated in the hair information collection device is connected by the Internet, by WLAN or another conventional way to a (for example a further) external data processing device, for example a computer, for example a cloud. In such a case the calculations can be performed for example by the (further) external data processing device, for example by the computer, and the result can be provided to the smartphone/tablet or the like and/or to the internal circuit device.

Further advantageous embodiments of the method will become clear from the description of the device, and vice versa.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A hair information collection device for providing information relating to the hair of a user, comprising:
    a device body having at least a first region and a second region configured such that the hair of the user is movable between the first region and the second region while in contact with the first region and the second region;
    at least one microphone arranged in or on the device body for detecting a noise during movement of the hair between the first region and the second region;
    a speed sensor circuit which is arranged in or on the device body and comprising at least one sensor for determining a value representing a speed of the device body; and
    an electronic circuit device arranged in or on the device body,
    wherein the electronic circuit device is coupled to the at least one microphone and the speed sensor circuit to receive the detected noise and the speed of the device body, to determine a hair condition information based on the detected noise and the speed of the device body; and
    wherein the electronic circuit device is configured to provide the hair condition information to the user.

2. The hair information collection device according to claim 1, wherein the device body is formed as a comb or as a brush, and wherein the first region and the second region comprise two adjacent comb teeth or two adjacent bristles of the brush.

3. The hair information collection device according to claim 1, wherein the electronic circuit device is configured to determine a recommendation based on the detected noise and the speed of the device body and to provide the recommendation to the user.

4. The hair information collection device according to claim 3, wherein the recommendation comprises at least one of a haircare product recommendation, a hairstyling product recommendation, and a hair treatment recommendation.

5. The hair information collection device according to claim 1, wherein the at least one microphone comprises a plurality of microphones.

6. The hair information collection device according to claim 1, wherein the at least one microphone is sealed in the device body.

7. The hair information collection device according to claim 1, wherein the electronic circuit device comprises a wireless data exchange device.

8. The hair information collection device according to claim 7 comprising:
    a display device,
    wherein the electronic circuit device is configured to transmit to the display device the information relating to the hair of the user by the data exchange device.

9. The hair information collection device according to claim 1, further comprising a camera for recording a digital image of the hair.

10. A method for providing information relating to the hair of a user, the method comprising the steps of:
    moving a hair information collection device according to claim 1 such that the hair of the user moves between the first region and a second region while in contact with the first region and the second region;
    detecting a noise by the at least one microphone and the speed of the device body by the speed sensor circuit during the movement of the device body; and
    providing the user with information regarding the hair based on the detected noise and the speed of the device body.

11. The method according to claim 10, further comprising the step of:
    determining at least one recommendation, based on the detected noise and the speed of the device body.

12. The method according to claim 11 wherein the at least one recommendation is further defined as a haircare product recommendation, a hairstyling product recommendation, and/or a hair treatment recommendation.

13. The method according to claim 10, further comprising the steps of:
transmitting the detected noise and the detected speed to an external data processing device; and
receiving the information provided by the external data processing device,
wherein the at least one piece of hair condition information is determined based on the detected noise and the speed by the external data processing device.

14. A hair information collection system for providing information relating to the hair of the user, comprising:
a device body having at least a first region and a second region configured such that the hair of the user is movable between the first region and the second region while in contact with the first region and the second region;
at least one microphone arranged in or on the device body for detecting a noise during movement of the hair between the first region and the second region;
an electronic circuit device arranged in or on the device body;
a data processing device with a housing;
a speed sensor circuit arranged in the housing of the data processing device and comprising at least one sensor for determining a value representing the speed of the data processing device;
wherein the device body is configured to be fixedly connected to the data processing device so that the speed of the data processing device is the same as the speed of the device body;
wherein the electronic circuit device is coupled to the at least one microphone to receive the detected noise;
wherein the data processing device is coupled to the speed sensor circuit to receive the speed of the device body, and wherein the data processing device is configured to determine a hair condition information based on the detected noise and the speed of the device body and provide the user with the hair condition information.

15. A method for providing information relating to the hair of a user, the method comprising the steps of:
moving a hair information collection system such that the hair of the user moves between the first region and a second region while in contact with the first region and the second region;
detecting a noise by the at least one microphone and the speed of the device body by the speed sensor circuit during the movement of the device body;
determining a hair condition information based on the noise and the speed of the device body; and
providing the user with the hair condition information.

16. The method according to claim 15, further comprising the step of determining at least one piece of hair condition information based on the detected noise and the speed of the device body.

17. The method according to claim 15, further comprising the step of determining at least one of a haircare product recommendation, a hairstyling product recommendation, and a hair treatment recommendation based on the detected noise and the speed of the device body.

18. The method according to claim 15, further comprising the steps of:
transmitting the detected noise and the detected speed to an external data processing device; and
receiving the information provided by the external data processing deice,
wherein the at least one piece of hair condition information is determined based on the detected noise and the speed by the external data processing device.

* * * * *